(12) United States Patent
Czop

(10) Patent No.: US 7,520,004 B2
(45) Date of Patent: Apr. 21, 2009

(54) COMBINED CUSHION AND PROTECTIVE COVER AND METHODS OF FORMING

(75) Inventor: Michael W. Czop, Fenton, MI (US)

(73) Assignee: Contour Fabricators, Inc., Fenton, MI (US)

( * ) Notice: Subject to any disclaimer, the term of this patent is extended or adjusted under 35 U.S.C. 154(b) by 197 days.

(21) Appl. No.: 11/492,723

(22) Filed: Jul. 25, 2006

(65) Prior Publication Data

US 2008/0023009 A1    Jan. 31, 2008

(51) Int. Cl.
*A47C 27/16* (2006.01)
(52) U.S. Cl. .................... 5/411; 5/601; 5/699; 5/740
(58) Field of Classification Search ............. 5/625–628, 5/722, 731, 737, 740, 655.9, 657, 640, 411, 5/601, 81.1 HS, 81.1 T, 699, 484, 502; 378/209; 108/90
See application file for complete search history.

(56) References Cited

U.S. PATENT DOCUMENTS

| | | | |
|---|---|---|---|
| 3,861,666 A | 1/1975 | Nishiyama et al. | |
| 4,484,571 A | 11/1984 | Velazquez | |
| 4,910,819 A | 3/1990 | Brown | |
| 4,991,242 A | 2/1991 | Brown | |
| 5,070,520 A | 12/1991 | Brown | |
| 5,121,514 A | 6/1992 | Rosane | |
| 5,189,746 A | 3/1993 | Horie | |
| 5,396,672 A | 3/1995 | Brown | |
| 5,701,619 A * | 12/1997 | Ullman | 5/625 |
| 5,860,174 A | 1/1999 | Failor | |
| 5,983,426 A | 11/1999 | Vanek et al. | |
| 6,128,796 A | 10/2000 | McCormick et al. | |
| 6,233,766 B1 * | 5/2001 | Ohman | 5/627 |
| 6,510,595 B2 | 1/2003 | Matsushima et al. | |
| 7,225,489 B1 * | 6/2007 | Frickey et al. | 5/723 |

FOREIGN PATENT DOCUMENTS

GB         2030448 A  *  4/1980

* cited by examiner

*Primary Examiner*—Michael Trettel
(74) *Attorney, Agent, or Firm*—John K. McCulloch

(57) ABSTRACT

A combined cushion and protective covering for a patient support having a patient-supporting surface comprises a central section having length and width dimensions corresponding substantially to corresponding dimensions of the support surface. Flaps which are unitary with the central section extend from the side edges of the central section a distance beyond the side edges of the support surface. The flaps are thinner than the central section so as to depend from the central section and lie alongside the patient-supporting surface. The central section and the flaps are formed simultaneously by compressing a block of cushioning material in such manner that the central section forms a pad or cushion unitarily joined at its opposite sides to the flaps. During the compression of the block to form the central pad and the flaps the external surfaces of the pad and flaps are heated to an extent sufficient to enable the surfaces of the pad and flaps to form a smooth, moisture proof skin.

20 Claims, 2 Drawing Sheets

COMBINED CUSHION AND PROTECTIVE COVER AND METHODS OF FORMING

This disclosure relates to a protective cover of the kind adapted to overlie a patient-supporting surface and provide cushioning for the patient and having flaps at opposite sides of the cover which depend from the central section to inhibit the unintentional admission of fluids to such surface.

BACKGROUND OF THE INVENTION

The protective covers disclosed herein are improvements over that disclosed in copending application Ser. No. 10/896,704, the disclosure of which is incorporated herein by reference.

A protective cover of the kind to which the invention relates has a central, relatively soft pad or cushion section corresponding substantially to the length and width dimensions of a supporting surface such as an imaging table on which a patient may be placed for the purpose of enabling diagnostic or other procedures to be performed. The surface of the table on which the patient is placed conventionally overlies electronic and other components which are utilized in the imaging or treatment of a patient supported atop the table. It frequently occurs that fluids from the patient or another source are admitted to the upper surface of the supporting table and, in some instances, such fluid contaminates the imaging apparatus housed below the support surface. In such event, both the support and imaging apparatus must be cleaned and, if the fluids contaminate the imaging apparatus, the table may be out of service for a substantial length of time.

Protective apparatus disclosed in the above identified patent application functions very well to prevent or minimize the problems associated with fluids collecting on or seeping through the upper surface of a patient support. However, such protective apparatus requires the inclusion of a waterproof coating, thereby necessitating the application and curing of the coating and the attendant cost of such coating and its application.

A conventional protective cover may have a center section or pad adapted to lie on the imaging table. Extending laterally from opposite side edges of the pad are flaps to provide for the attachment of patient restraining straps and to form a barrier to the admission of fluids to the surface of the table. These flaps conventionally are added to the central section as a separate operation, thereby requiring materials and operations in addition to those involved in the production of the pad.

A protective cover constructed in accordance with the disclosed embodiment avoids the necessity of a coating, as well as its application, but does not sacrifice the waterproof nature of the protective apparatus. The protective cover according to the invention also enables the central pad and unitary flaps to be formed simultaneously.

SUMMARY OF THE DISCLOSURE

The disclosed protective cover comprises, in one embodiment, a unitary block of cushioning foam material that has been permanently deformed by compression to produce a relatively thick central section adapted to support a person upon the upper surface of a table, gurney, or other patient-supporting structure. The formation of the central section is accompanied by the simultaneous formation of relatively thin, flexible flaps which may flank the central section and extend from opposite sides thereof a distance sufficient to enable the flaps to depend and lie alongside the patient-supporting structure. The central section and the flaps are formed simultaneously and, therefore, are unitary.

The block of cushioning material is permanently deformed in a press of conventional construction having mold components by means of which a desired shape is imparted to the finished product. The compression of the cushioning material is accompanied by the application of heat, thereby enabling the material at the surfaces of the central section and the flaps to become somewhat fluent so that, following completion of the compression stage and cooling, all surfaces of the central section and the flaps have either a smooth or textured skin which is moisture proof.

In all embodiments the flaps extend from opposite sides of the central section of the cover. In some instances the level of the flaps corresponds substantially to that of the lower surface of the central section, whereas in other embodiments the level of the flaps corresponds substantially to that of the upper surface of the central section or at a selected level between the upper and lower surfaces of the central section.

In one embodiment the block of cushioning material has multiple layers forming a sandwich wherein one layer of material is interposed between other layers of cushioning material. One of the layers preferably has a stiffness different from that of the other two sections.

In one sandwich embodiment the length of the center layer corresponds to the length of the two outer layers, but has a width less than that of the two outer layers. The two outer layers, however, are of uniform width so that, when the unit is subjected to compressive deformation, the opposite sides of the upper and lower layers will wrap around the opposite sides of the middle layer and form the flaps in the same manner as has been described.

THE DRAWINGS

Several preferred embodiments of a combined protective cover and cushion construction are illustrated in the accompanying drawings wherein.

DETAILED DESCRIPTION

Figure 1:
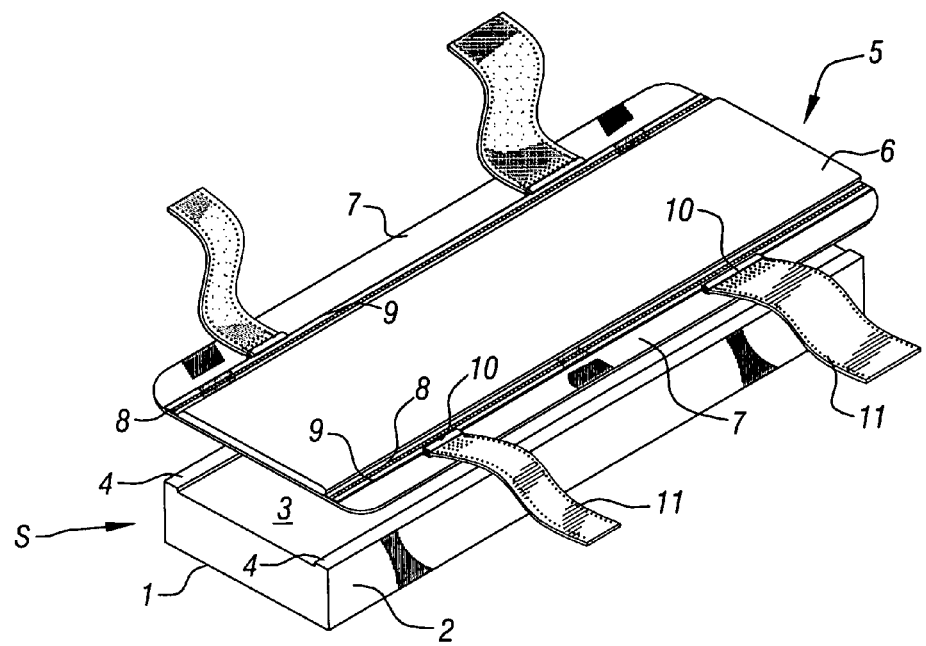
FIG. 1 is an isometric view of the upper surface of a patient-supporting table underlying a combined cushioned and protective cover, the cover having laterally extending flaps and patient-restraining straps.

All of the disclosed combined cushion and protective covers are adapted for use in conjunction with a typical patient support S corresponding substantially to that shown in FIG. 1 and comprising a rectangular member 1 having side walls 2 and an upper surface 3. The upper surface may terminate at its opposite sides in upstanding bars 4 to help position a patient on the support.

FIG. 1 illustrates a combined cushion and protective cover 5 in a position to overlie and rest upon the upper surface 3 of the support S. The cover 5 has a central section forming a cushion or pad 6 from opposite sides of which extend flaps 7. Secured to the flaps adjacent the pad section 6 is a pair of anchor strips 8 terminating at one edge in a bead 9 that is adapted to accommodate a slideable anchor member 10 secured to one end of a flexible strap 11 as is shown in more detail in the aforementioned application.

The central section or pad 6 has length and width dimensions corresponding substantially to those of the upper surface 3 of the support S. The flaps 7, however, extend beyond the pad 6 a distance sufficient to project beyond the side edges of the surface 3 of the support S. The flaps 7 are of such flexibility as normally to assume positions depending from the central pad 6 and overlie at least the upper portion of the sides 2 of the support S. Although each flap is shown as being of uniform thickness, each flap could be slightly thicker at its perimeter than elsewhere to resist buckling of the flap in use.

Figure 2:
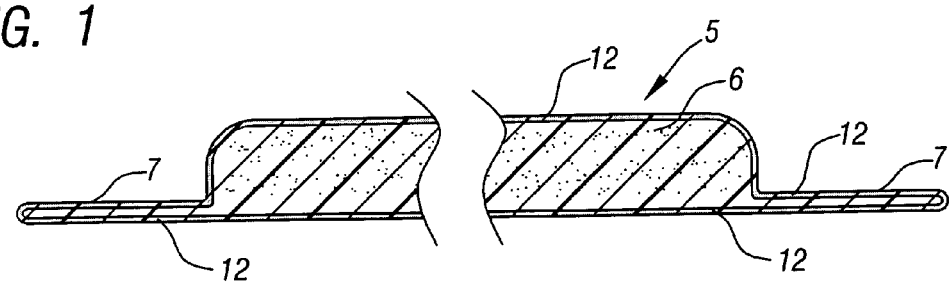
FIG. 2 is a transverse sectional view, on a greatly enlarged scale, illustrating a protective cover having a central cushion section and laterally extending flaps at a level corresponding substantially to that of the lower surface of the cushioning section.

The structure of the combined cushion and protective cover 5 shown in FIG. 1 is illustrated in more detail in FIG. 2. The central pad 6 has a desired thickness, such as 1 inch, which is significantly greater than the thickness of the flaps 7, and the flaps are of substantially uniform thickness, such as ⅛ inch. The central pad 6 and the flaps 7 are formed simultaneously in a mold (not shown). The cover 5 is formed from a rectangular block of foam cushioning material, such as open or closed cell ethyl vinyl acetate or polyethylene, or any other suitable material. The block is placed in a mold (not shown) supported on the base of a press (not shown). The press is conventional and includes an upper platen which carries a mold vertically movable toward and away from the base. The molds carried by the press have cavities corresponding to the final configuration of the cushion/cover 5 that is to be formed. When the platen moves toward the base on which the block of cushioning material is positioned, the compressive force imposed on the block will be sufficient to deform the block permanently to produce a selected configuration, such as that shown in FIG. 2.

The central pad 6 and the flaps 7 are formed simultaneously. During the compression of the block of cushioning material, the mold will be heated in a conventional manner and heat from the mold will be transferred to all external surfaces of the cushion/cover 5 so as to cause the outer surface of the member to become at least partially fluent or flowable, whereupon a thin portion of the surfaces of the member 5 will form a moisture proof skin. The skin is indicated by the reference character 12. The skin not only forms a moisture proof exterior for all parts of the member 5, but also provides either a textured or smooth surface. If the surface is smooth it facilitates the sliding of a patient onto and off the support surface 3.

Although the lower surface of the flap 7 illustrated in FIG. 2 is substantially coplanar with the lower surface of the central pad 6, turning the member 5 over will locate the flaps at a level corresponding to the then upper surface of the pad.

Figure 3:
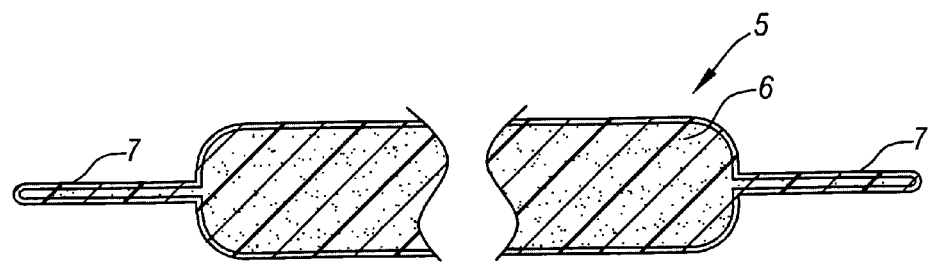
FIG. 3 is a view similar to FIG. 2, but illustrating the laterally extending flaps as occupying a level between the levels of the upper and lower surfaces of the cushioning section.

The embodiment illustrated in FIG. 3 is the same as that shown in FIG. 2 with the exception that the flaps 7 occupy a position at a selected level between the upper and lower surfaces of the central pad 6. The embodiment of FIG. 3 is formed in the same way as that shown in FIG. 2 with the exception, of course, that the configuration of the mold in the press conforms to the configuration illustrated in FIG. 3.

Figure 4:
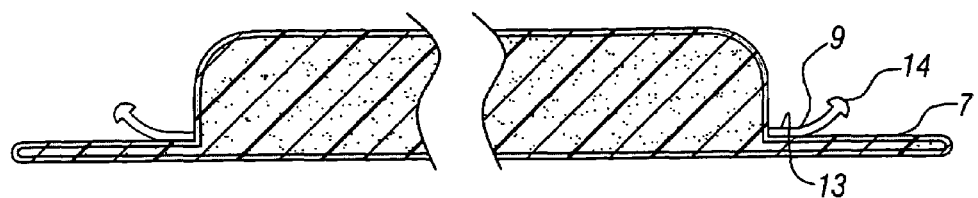
FIG. 4 is a view corresponding to FIG. 2, but including retaining means for patient-restraining straps.

The embodiment shown in FIG. 4 is the same as that shown in FIG. 2, but includes the anchor member 9. The anchor member has an elongate strip 13 formed of an appropriate plastic or fabric material which is secured to the upper surface of the flange 7 by stitching, adhesive, or in any other suitable way. Depending on the materials from which the parts are made, the strip 13 could be fused or welded to the flap. The strip 13 terminates in a bead 14 which cooperates with the anchor member 10 to effect a sliding connection with one of the straps 11, as is discussed at some length in the aforementioned application. It will be clear from FIG. 4 that the attachment of the strip 13 to the flap 7 is such as to enable the bead 14 to occupy a position above the level of the upper surface of the flap 7, thereby facilitating the connection of the bead to and from the anchor member 10. Although the strip 13 and the bead 14 are shown as being adhered to the upper surface of the flap, they could be adhered, if desired, to the lower surface.

Figure 5:
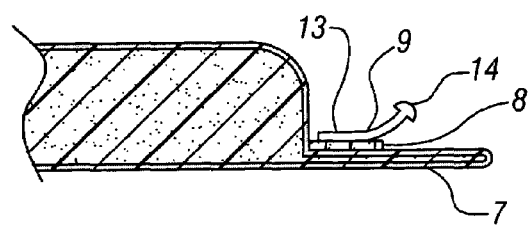
FIG. 5 is a fragmentary view similar to FIG. 4 illustrating an alternate way of securing the patient-restraining straps to the flaps.

The embodiment shown in FIG. 5 is the same as that shown in FIG. 4 with the exception that the FIG. 5 embodiment includes the attaching strip 8 interposed between the flap 7 and the strip 13. Again, the attaching strip 8 may be formed of fabric, plastic, or any other suitable material and adhered to the flap and the strip 13 by stitching, adhesive, or fusion, depending on the materials used in the construction.

Figure 6:
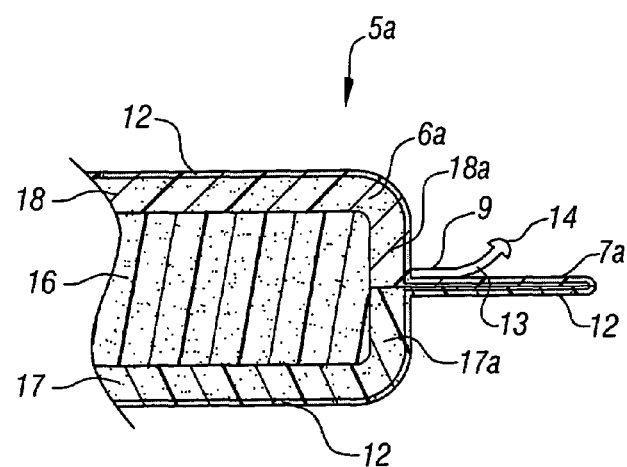
FIG. 6 is a fragmentary view illustrating a combined cushion and protective cover composed of a sandwich of cushioning materials.

FIG. 6 illustrates a different form of cushion/cover 5a wherein the central section or pad 6a comprises a sandwich composed of three separate layers 16, 17, and 18 with the layer 16 occupying a position between the layers 17 and 18. In the production of the member 5a, the layer 16 is placed between the other two layers so that opposite sides 17a, 18a of the latter layers project beyond the side edges of the layer 16. The assembly then is deformed by compression in the manner described above so that the projecting sides 17a and 18a wrap around the opposite side edges of the layer 16. The outboard edges of the layers 17 and 18 are compressed to form the flap 7a in the same manner as has been described.

Following the production of the member 5a each of the layers 16, 17, and 18, may be of different stiffness, i.e., each may have a different resistance to the compression. Preferably, the stiffness of the outer layers 17 and 18 is the same and the stiffness of the inner layer 16 is less than that of the other two layers, thereby resulting in a cushion on which a patient may lie that is somewhat softer than one in which the stiffness of all of the layers is the same. Alternatively, the stiffness of each of the layers may be different. The stiffness may be controlled by the selection of appropriate materials prior to molding, or by using open or closed cell foam for one or more layers.

In the formation of the embodiment shown in FIG. 6, a skin 12 is formed on all surfaces of the member in the manner described above.

In each of the disclosed embodiments the compressive deformation of the material forming the flaps is such as virtually to eliminate all cells of the foam. Consequently, the flaps have significant resistance to tearing.

The disclosed embodiments are representative of preferred forms of the invention, but are intended to be illustrative rather than definitive thereof. The invention is defined in the claims.

I claim:

1. A combined protective cover and cushion construction adapted for use with a support having an upper surface of selected length and width, said construction comprising a first section of such length and width as to overlie and form a cushion for said surface, and a pair of flaps flanking and extending beyond opposite sides of said first section, said first section and said flaps being unitary and formed from cushioning material permanently deformed to different thicknesses, said flaps having a thickness less than that of said first section, said first section and each of said flaps having a smooth or textured moisture proof skin formed during the deformation of said cushioning material.

2. The construction according to claim 1 wherein said first section and each of said flaps have upper and lower surfaces, one surface of said first section being substantially coplanar with a surface of each of said flaps.

3. The construction according to claim 1 wherein said first section and each of said flaps have upper and lower surfaces, the lower surfaces of said first section and said flaps being substantially coplanar.

4. The construction according to claim 1 wherein said first section and said flaps are formed from foam material.

5. The construction according to claim 1 wherein said first section comprises a plurality of individual layers of cushioning material arranged in overlying relation.

6. The construction according to claim 5 wherein all of said layers are composed of identical cushioning material.

7. The construction according to claim 5 wherein not all of said layers are composed of identical cushioning material.

8. The construction according to claim 5 wherein at least one of said layers has a width less than that of an adjacent layer.

9. The construction according to claim 5 wherein said first section is formed of three of said layers arranged in sandwich form and wherein two of said layers flank the third layer, at least one of said layers having less resistance to compression than the others of said layers.

10. The construction according to claim 9 wherein said one of said layers is sandwiched between the other two of said layers.

11. A combined protective cover and cushion construction adapted for use with a support having an upper surface of selected length and width, said construction comprising a first section of such length and width as to overlie and form a cushion for said surface, and a pair of flaps flanking and extending beyond opposite sides of said first section, said first section and said flaps being unitary and formed from cushioning material permanently deformed to different thickness, said flaps having a thickness less than that of said first section, said first section and each of said flaps having upper and lower surfaces, the upper and lower surfaces of said flaps being at a level between the upper and lower surfaces of said first section.

12. A protective cover and cushion comprising a central section having length, width, and thickness dimensions, and a pair of flaps flanking and extending beyond opposite sides of said central section, said central section and each of said flaps having upper and lower surfaces, said central section and said flaps being unitary and formed from deformable, compressible, cushioning material permanently deformed to different thicknesses, the thickness of each of said flaps being sufficiently less than that of said central section as to enable said flaps to be of such flexibility as to depend from said central section.

13. The construction according to claim 12 wherein the upper and lower surfaces of said central section and said flaps have a selected smooth or textured moisture proof skin formed from said cushioning material.

14. A method of forming a cushioned, protective cover for a surface having selected length and width dimensions, said cover having opposite surfaces and opposite side edges, said method comprising permanently deforming by compression a first section of a block of compressible material and inward of said side edges to a predetermined thickness; and permanently deforming the side edges of said block adjacent said first section to a thickness less than that of said first section, thereby forming flaps at opposite sides of said first section, said flaps being of such thickness and flexibility as to be capable of assuming a depending position at said opposite side edges of said first section.

15. The method according to claim 14 wherein the deformation of said first section and said side edges of said block occurs simultaneously.

16. The method according to claim 14 including heating and subsequently cooling said opposite surfaces of said block during compression of said first section and said opposite side edges to such an extent as to cause said opposite surfaces to form a textured or smooth skin.

17. The method according to claim 14 wherein said first section is composed of a plurality of overlying layers of cushioning material.

18. The method according to claim 17 wherein there are three of said layers.

19. The method according to claim 18 wherein at least one of said layers is formed of cushioning material having a resistance to compression less than that of another of said layers.

20. The method according to claim 19 including sandwiching said one of said members between the others of said members prior to said deformation.

* * * * *